US012127548B2

(12) United States Patent
Ortega et al.

(10) Patent No.: US 12,127,548 B2
(45) Date of Patent: Oct. 29, 2024

(54) MEDICAL DEVICE INCLUDING AN ULTRASONIC EMITTER FOR INFESTATION AVOIDANCE

(71) Applicant: Fresenius Medical Care Holdings, Inc., Waltham, MA (US)

(72) Inventors: Anthony Ortega, Antioch, CA (US); John Jacob, Tracy, CA (US); Paramvir Singh Virk, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 137 days.

(21) Appl. No.: 17/723,745

(22) Filed: Apr. 19, 2022

(65) Prior Publication Data

US 2023/0329224 A1    Oct. 19, 2023

(51) Int. Cl.
*A01M 29/18* (2011.01)
*A61M 1/28* (2006.01)

(52) U.S. Cl.
CPC .............. *A01M 29/18* (2013.01); *A61M 1/28* (2013.01)

(58) Field of Classification Search
CPC ........ A61M 1/28; A61M 29/18; A61M 29/16; A01M 29/18; A01M 29/16
USPC ................. 43/107, 132.1; 116/22 A; 367/139
See application file for complete search history.

(56) References Cited

U.S. PATENT DOCUMENTS

| | | | | | |
|---|---|---|---|---|---|
| 3,879,702 | A | * | 4/1975 | Mancone | A01M 29/18 43/124 |
| 3,886,492 | A | * | 5/1975 | White | A01M 29/18 43/132.1 |
| 3,931,865 | A | * | 1/1976 | Levitt | A01M 29/18 43/107 |
| 4,178,578 | A | * | 12/1979 | Hall | G10K 9/22 43/124 |
| 4,392,215 | A | * | 7/1983 | Hall | A01M 29/18 367/139 |
| 4,484,315 | A | * | 11/1984 | Hall | B06B 1/0284 43/124 |
| 4,562,561 | A | * | 12/1985 | Ackley | A01M 29/18 367/139 |
| 4,566,085 | A | * | 1/1986 | Weinberg | B06B 1/0276 116/22 A |

(Continued)

FOREIGN PATENT DOCUMENTS

CN            105532634 A  *  5/2016  ............ A01M 29/18

OTHER PUBLICATIONS

Fredericks Jim, and Henriksen, Missy, "How to control pests in health care facilities", Feb. 4, 2015, Health Facilities Management, URL: <https://www.hfmmagazine.com/articles/1478-how-to-control-pests-in-health-care-facilities> (Year: 2015).*

(Continued)

*Primary Examiner* — Darren W Ark
*Assistant Examiner* — Zoe Tam Tran
(74) *Attorney, Agent, or Firm* — KDW Firm PLLC

(57) ABSTRACT

A medical device configured to prevent bug infestation is disclosed. The medical device may be a dialysis machine (e.g., a peritoneal dialysis machine) for conducting dialysis treatments. The medical device (e.g., dialysis machine) including an ultrasonic generator and emitter arranged and configured to emit an ultrasonic high frequency sound to prevent bug infestation.

20 Claims, 5 Drawing Sheets

(56) References Cited

U.S. PATENT DOCUMENTS

| | | | | | |
|---|---|---|---|---|---|
| 4,616,351 | A | * | 10/1986 | Hall | B06B 1/0276 |
| | | | | | 43/124 |
| 4,999,818 | A | * | 3/1991 | Malleolo | A01M 29/18 |
| | | | | | 367/139 |
| 5,598,379 | A | * | 1/1997 | Malleolo | A01M 29/18 |
| | | | | | 340/384.2 |
| 5,832,657 | A | * | 11/1998 | Jan | A01M 31/002 |
| | | | | | 116/22 A |
| 5,896,696 | A | * | 4/1999 | Stokes | A01M 1/226 |
| | | | | | 43/132.1 |
| 6,301,194 | B1 | * | 10/2001 | Cauchy | A01M 29/18 |
| | | | | | 119/719 |
| 6,570,494 | B1 | * | 5/2003 | Leftridge, Sr. | A01M 29/18 |
| | | | | | 43/132.1 |
| 6,710,705 | B1 | * | 3/2004 | Smith | A01M 31/002 |
| | | | | | 340/384.73 |
| 6,882,594 | B1 | * | 4/2005 | Pujolas | A01M 29/28 |
| | | | | | 43/132.1 |
| 7,271,706 | B2 | * | 9/2007 | Lee | A01M 1/24 |
| | | | | | 43/132.1 |
| 7,948,386 | B2 | * | 5/2011 | Weiser | A01M 29/18 |
| | | | | | 340/573.2 |
| 2009/0034369 | A1 | * | 2/2009 | Hill | A01M 29/18 |
| | | | | | 367/139 |
| 2009/0213217 | A1 | * | 8/2009 | Ko | A01M 29/18 |
| | | | | | 348/143 |
| 2011/0017665 | A1 | * | 1/2011 | Updyke | A61M 1/28 |
| | | | | | 210/96.2 |
| 2013/0077446 | A1 | * | 3/2013 | Kasper | A01M 29/18 |
| | | | | | 367/139 |
| 2014/0016439 | A1 | * | 1/2014 | Nakayama | A01M 29/18 |
| | | | | | 367/139 |
| 2014/0098643 | A1 | * | 4/2014 | Power | A01M 29/18 |
| | | | | | 367/139 |
| 2014/0209040 | A1 | * | 7/2014 | Kinzie | F03D 80/00 |
| | | | | | 119/719 |
| 2015/0128877 | A1 | | 5/2015 | McIntyre | |
| 2015/0230450 | A1 | * | 8/2015 | Norris | A01M 31/002 |
| | | | | | 367/139 |
| 2022/0248659 | A1 | * | 8/2022 | Salter | A01M 29/18 |

OTHER PUBLICATIONS

International Search Report and Written Opinion for the International Application No. PCT/US2023/014880, mailed May 22, 2023, 12 pages.

* cited by examiner

MEDICAL DEVICE INCLUDING AN ULTRASONIC EMITTER FOR INFESTATION AVOIDANCE

FIELD OF THE DISCLOSURE

The disclosure generally relates to medical devices, and more particularly to a medical device, such as, for example, a dialysis machine, including an ultrasonic generator and emitter arranged and configured to emit an ultrasonic high frequency sound to prevent bug infestation.

BACKGROUND

Medical devices, such as dialysis machines, are known for use in the treatment of renal disease. The two principal dialysis methods are hemodialysis (HD) and peritoneal dialysis (PD). During HD, the patient's blood is passed through a dialyzer of an HD machine while also passing dialysate through the dialyzer. A semi-permeable membrane in the dialyzer separates the blood from the dialysate within the dialyzer and allows diffusion and osmosis exchanges to take place between the dialysate and the blood stream. During PD, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream.

A dialysis machine, such as a PD machine or cycler (used interchangeably herein without the intent to limit), may include one or more containers (e.g., bags) containing a fluid (e.g., a dialysate) for patient infusion. In PD machines, for example, tubing as fluid lines are inserted into an abdomen of a patient for flowing fresh dialysate and removing used dialysate, waste, and excess fluid. In a PD machine, fresh dialysate may travel from the one or more containers, through tubing and into a disposable cartridge or cassette (used interchangeably without intent to limit) that may be inserted into a port located in the PD machine. During use, one or more pumps or actuators positioned within the PD machine interact with the disposable cassette to move fluid from the one or more containers to the patient.

Automated PD machines, also called PD cyclers, are designed to control the entire PD process so that it can be performed at home, usually overnight, without clinical staff in attendance. Home hemodialysis machines are also known and provide for performing hemodialysis treatments in a patient's home.

During its lifespan, dialysis machines may become infested with bugs such as, for example, insects, spiders, roaches, etc. Bug infestation is a particular problem associated with PD machines since PD machines are often used in a patient's home.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a medical device is disclosed. For example, in one embodiment, a dialysis system and/or dialysis machine for conducting a dialysis treatment is disclosed. In one embodiment, the medical device includes a housing including an ultrasonic high frequency generator and emitter arranged and configured to generate and transmit an ultrasonic high frequency sound to repel bugs.

In one embodiment, the emitted ultrasonic high frequency sound is inaudible to humans but audible by bugs.

In one embodiment, the emitted ultrasonic high frequency sound discourages bugs from entering the housing of the medical device.

In one embodiment, the emitted ultrasonic high frequency sound is between 20 kHz and 120 kHz.

In one embodiment, the ultrasonic high frequency generator and emitter is an electronic circuit.

In one embodiment, the electronic circuit is printed on a stand-alone circuit board arranged and configured to be coupled to an alternate circuit board of the medical device.

In one embodiment, the ultrasonic high frequency generator and emitter is continuously powered so that the ultrasonic high frequency generator and emitter is continuously active and thus continuously emitting the ultrasonic high frequency sound.

In one embodiment, the ultrasonic high frequency generator and emitter is coupled to a rechargeable battery.

In one embodiment, the rechargeable battery is arranged and configured to be charged by the medical device when the medical device is powered ON.

In one embodiment, the ultrasonic high frequency generator and emitter is coupled to a controller of the medical device so that a frequency of the emitted ultrasonic high frequency sound is adjustable.

In one embodiment, the medical device is a dialysis machine arranged and configured for conducting a dialysis treatment.

A method of repelling bug infestation in a medical device is also disclosed. In one embodiment, the method includes emitting, from a housing of the medical device, an ultrasonic high frequency sound to repel bugs.

In one embodiment, the emitted ultrasonic high frequency sound is inaudible to humans but audible by bugs.

In one embodiment, the emitted ultrasonic high frequency sound discourages bugs from entering the housing of the medical device.

In one embodiment, the emitted ultrasonic high frequency sound is between 20 kHz and 120 kHz.

In one embodiment, the emitted ultrasonic high frequency sound is continuously active so that the emitted ultrasonic high frequency sound is being continuously emitted.

In one embodiment, the method further includes adjusting a frequency of the emitted ultrasonic high frequency sound.

In one embodiment, the medical device is a dialysis machine, and the emitted ultrasonic high frequency sound discourages bugs from entering the housing of the dialysis machine.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
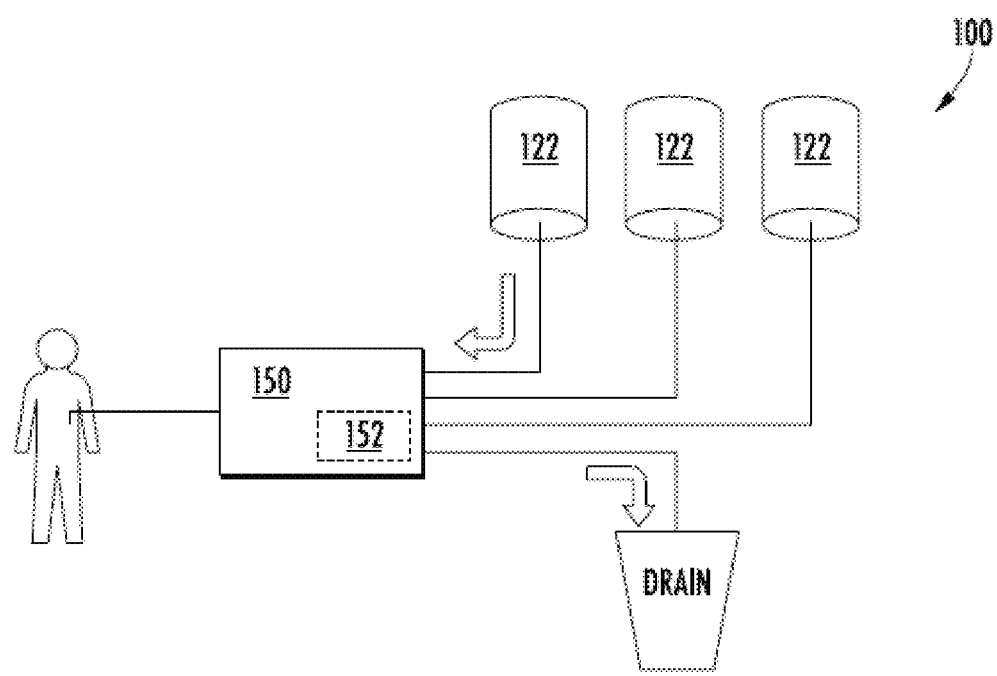
FIG. 1 illustrates an example of an embodiment of a dialysis system.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of systems and methods arranged and configured to prevent bug infestation in a dialysis machine will now be described. It will be appreciated that while a particular embodiment of a medical device, namely, a PD machine, will be shown and described, the concepts of the present disclosure are equally applicable to other medical devices, including other dialysis machines, such as other PD machines and/or HD machines. As such, the present disclosure should not be limited to any particular type of medical device or any particular type of dialysis machine unless explicitly claimed.

In accordance with one or more features of the present disclosure, a medical device such as, for example, a dialysis machine such as, for example, a PD machine, may include an ultrasonic generator and emitter such as, for example, a circuit arranged and configured to generate and emit an ultrasonic high frequency sound that is inaudible by humans but repels bugs such as, for example, insects, spiders, roaches, etc. In use, by generating and emitting a high frequency sound wave, bugs will stay away from the medical device (e.g., dialysis machine) thereby avoiding bug infestation.

Referring to FIG. 1, a dialysis system 100 may include a PD machine 150, for flowing fresh dialysate into a patient and draining used dialysate out of the patient. During treatment, a volume of dialysate may enter the patient's abdomen and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the used dialysate may be flowed out of the patient's abdomen and purged to a drain connected to the tubing, e.g., the drain line. This exchange of fresh dialysate and used dialysate after a dwell time may occur for several cycles depending on the patient's treatment regimen.

One or more dialysate sources may be connected to the dialysis machine 150. In some embodiments, as illustrated, the dialysate source(s) may be dialysate bags 122 that are disposed near the PD machine 150. In an embodiment, the dialysate bags 122 may be hung which may improve air content management as any air content is disposed by gravity to a top portion of the dialysate bag 122. Additionally, and/or alternatively, the dialysate bags 122 may be disposed on shelves below or near the PD machine 150. Valves may be attached to a bottom portion of the dialysate bags 122 so fluid is drawn out and air content delivery is minimized. In one embodiment, as shown, dialysate from the dialysate bags 122 may be transferred to the patient through a warming pouch, a heating chamber, or the like 152 (used interchangeably without the intent to limit) formed in the dialysis machine 150. When the dialysate has reached a predetermined temperature (e.g., approximately 98°-100° F., 37° C.) in the heating chamber 152, the dialysate may be flowed into the patient.

In one embodiment, the dialysate bags 122 may be connected to a cassette, which may be insertable into the dialysis machine 150. In use, the cassette may be connected to dialysate bag lines, which may be used to pass dialysate from dialysate bags 122 to the cassette. In use, the cassette may be disposable. Alternatively, the cassette may be reusable. In addition, a patient line and a drain line may be connected or associated with the cassette. The patient line may be connected to a patient's abdomen via a catheter and may be used to pass dialysate back and forth between the cassette and the patient's peritoneal cavity during use. The drain line may be connected to a drain or drain receptacle and may be used to pass dialysate from the cassette to the drain or drain receptacle during use. Although the system described herein is discussed principally in connection with the use of dialysate bags as the dialysate source, it is noted that, in other embodiments, different dialysate sources may be used. For example, in other embodiments, the dialysate source may include one or more containers in which dialysate is mixed and/or otherwise prepared at the PD cycler, see, e.g., U.S. Pat. No. 9,585,810 to Jenson et al., entitled "Systems and Methods for Delivery of Peritoneal Dialysis (PD) Solutions with Integrated Inter-chamber Diffuser," and U.S. Pat. No. 10,076,599 to Eyrard et al., entitled "Dry Peritoneal Dialysis Concentrate System," which are incorporated by reference herein in their entireties.

Figure 2:
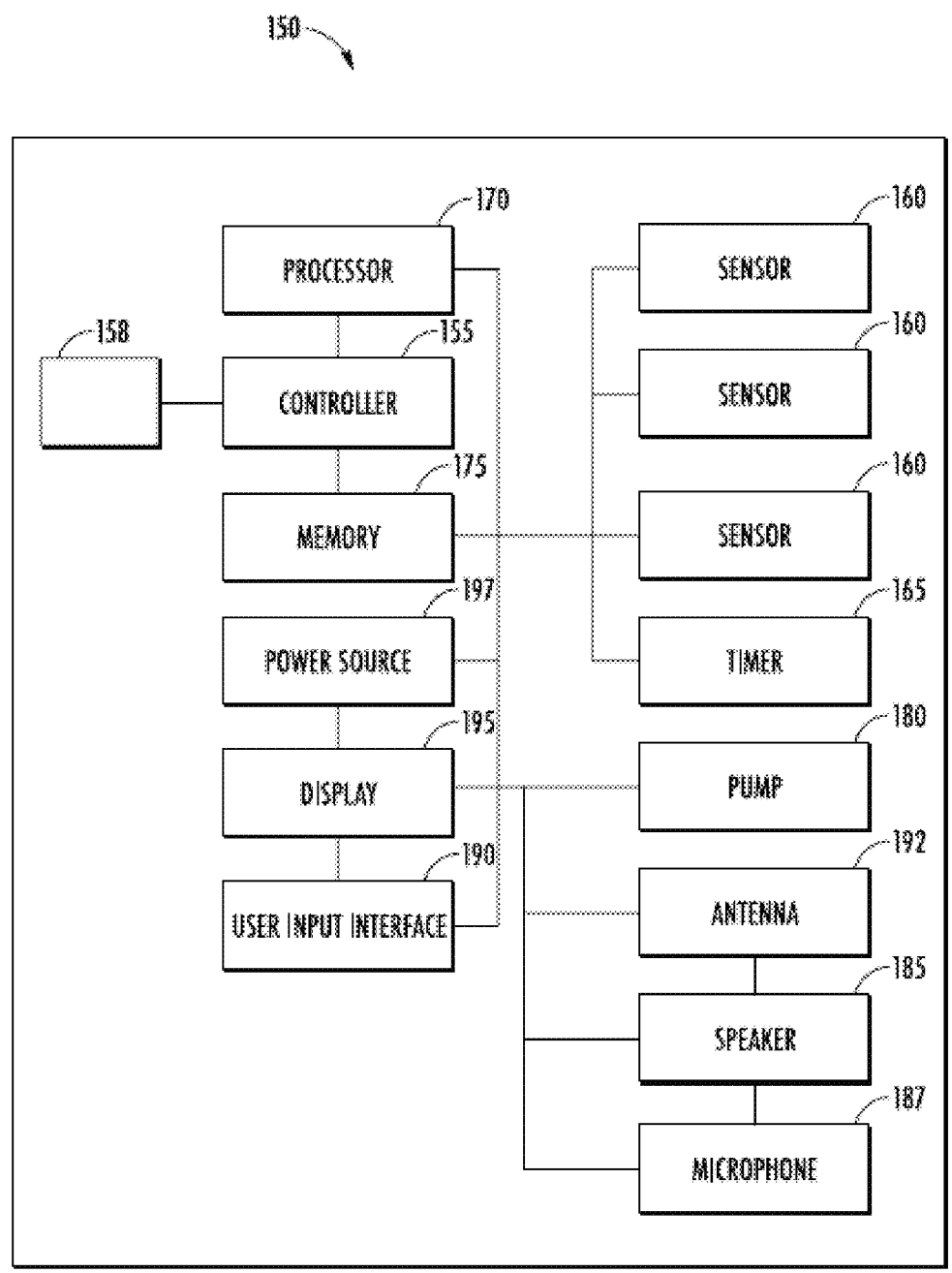
FIG. 2 is a block diagram illustrating an example of an embodiment of a dialysis machine and a controller.

Referring to FIG. 2, a schematic of an exemplary embodiment of a dialysis machine such as, for example, dialysis machine 150 and a controller 155 in accordance with the present disclosure are shown. The machine 150 may be a home dialysis machine, e.g., a PD machine, for performing a dialysis treatment on a patient, and may be included in the system 100 described above with respect to FIG. 1. The controller 155 may automatically control execution of a treatment function during a course of dialysis treatment. The controller 155 may be operatively connected to the sensors 160 and deliver a signal to execute a treatment function (e.g., transferring dialysate from the dialysate bag 122 through the heating chamber 152 and then to the patient), or a course of treatment associated with various treatment systems. In some embodiments, a timer 165 may be included for timing triggering of the sensors 160.

In some embodiments, the machine 150 may also include a processor 170, and memory 175, the controller 155, the processor 170, and/or the memory 175, or combinations thereof of the machine 150, may receive signals from the sensor(s) 160 indicating various parameters. Each fluid bag (e.g., the dialysate bags 122) may contain an approximate amount of dialysate, such that "approximate amount" may be defined as a 3L fluid bag containing 3000 to 3150 mL, a 5L fluid bag containing 5000 to 5250 mL, and a 6L fluid bag containing 6000 to 6300 mL. The controller 155 may also detect connection of all fluid bags 122 connected.

Communication between the controller 155 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In some embodiments, the dialysis machine 150 may include at least one pump 180 operatively connected to the controller 155. During a treatment operation, the controller 155 may control the pump 180 for pumping fluid, e.g., fresh and spent dialysate, to and from a patient. For example, the pump 180 may transfer dialysate from the dialysate bag 122 through, for example, a cassette insertable into a port or a compartment formed in the dialysis machine, to the heating chamber 152 prior to transferring the dialysis to the patient. In an embodiment, the pump 180 may be a peristaltic pump. The controller 155 may also be operatively connected to a speaker 185 and a microphone 187 disposed in the machine 150. A user input interface 190 may include a combination of hardware and software components that allow the controller 155 to communicate with an external entity, such as a patient or other user. These components may be configured to receive information from actions such as physical movement or gestures and verbal intonation. In some embodiments, the components of the user input interface 190 may provide information to external entities. Examples of the components that may be employed within the user input interface 190 include keypads, buttons, microphones, touch screens, gesture recognition devices, display screens, and speakers. The machine 150 may also be wirelessly connectable via an antenna 192 for remote communication. The machine 150 may also include a display 195 and a power source 197.

As shown in FIG. 2, the sensors 160 may be included for monitoring parameters and may be operatively connected to at least the controller 155, the processor 170, and/or the memory 175, or combinations thereof. The processor 170 may be configured to execute an operating system, which may provide platform services to application software, e.g., for operating the dialysis machine 150. These platform services may include inter-process and network communication, file system management and standard database manipulation. One or more of many operating systems may be used, and examples are not limited to any particular operating system or operating system characteristic. In some examples, the processor 170 may be configured to execute a real-time operating system (RTOS), such as RTLinux, or a non-real time operating system, such as BSD or GNU/Linux.

According to a variety of examples, the processor 170 may be a commercially available processor such as a processor manufactured by INTEL, AMD, MOTOROLA, and FREESCALE. However, the processor 170 may be any type of processor, multiprocessor or controller, whether commercially available or specially manufactured. For instance, according to one example, the processor 170 may include an MPC823 microprocessor manufactured by MOTOROLA.

The memory 175 may include a computer readable and writeable nonvolatile data storage medium configured to store non-transitory instructions and data. In addition, the memory 175 may include a processor memory that stores data during operation of the processor 170. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 175 may include executable programs or other code that may be executed by the processor 170. The instructions may be persistently stored as encoded signals, and the instructions may cause the processor 170 to perform the functions described herein. The memory 175 may include information that is recorded, on or in, the medium, and this information may be processed by the processor 170 during execution of instructions. The memory 175 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 155.

The sensor(s) 160 may include a pressure sensor for monitoring fluid pressure of the machine 150, although the sensors 160 may also include any of a heart rate sensor, a respiration sensor, a temperature sensor, a weight sensor, an air sensor, a video sensor, a thermal imaging sensor, an electroencephalogram sensor, a motion sensor, an audio sensor, an accelerometer, a capacitance sensor, or any other suitable sensor. It is appreciated that the sensors 160 may include sensors with varying sampling rates, including wireless sensors.

The controller 155 may be disposed in the machine 150 or may be coupled to the machine 150 via a communication port or wireless communication links, shown schematically as communication element 158. According to various examples, the communication element 158 may support a variety of one or more standards and protocols, examples of which include USB, Wi-Fi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 150, the controller 155 may be operatively connected to any of the sensors 160, the pump 180, and the like. The controller 155 may communicate control signals or triggering voltages to the components of the machine 150. As discussed, exemplary embodiments of the controller 155 may include wireless communication interfaces. The controller 155 may detect remote devices to determine if any remote sensors are available to augment any sensor data being used to evaluate the patient.

Figure 3A:
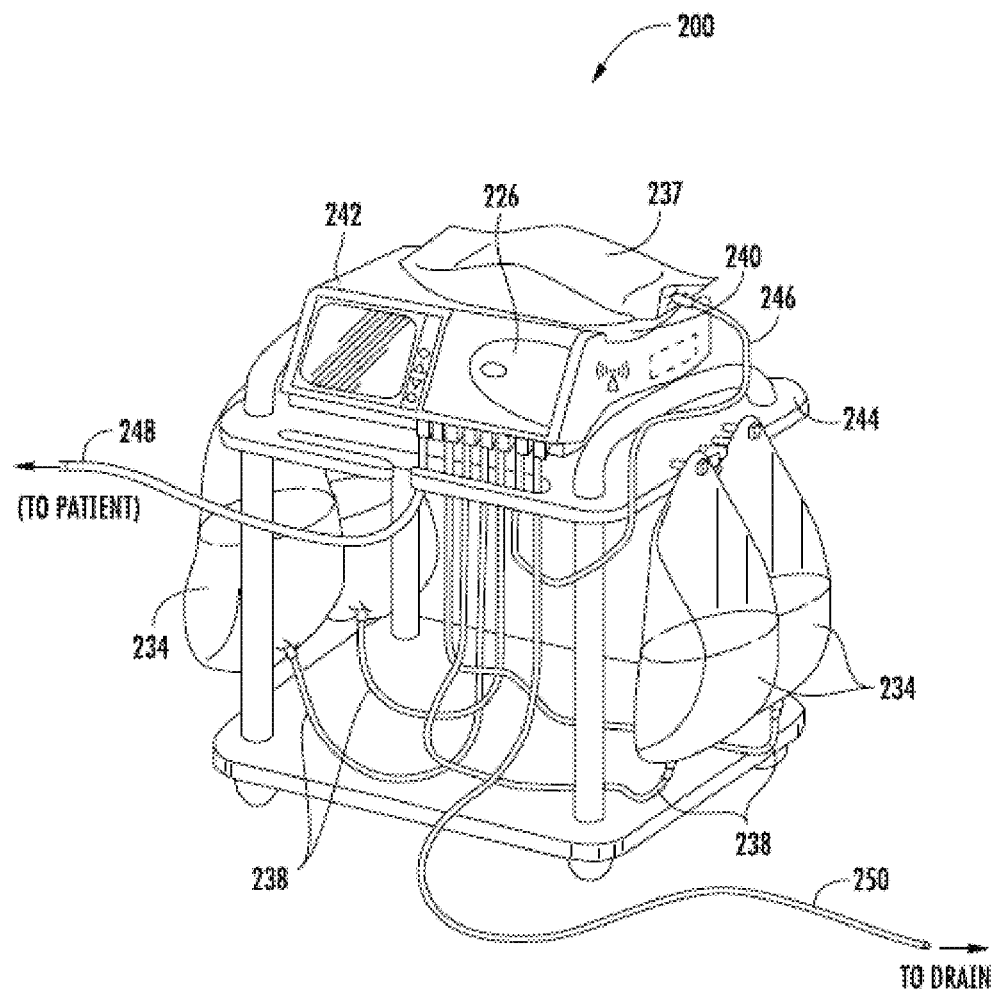
FIGS. 3A and 3B illustrate an example of an embodiment of a dialysis machine that can be used in the dialysis system of FIG. 1.
Figure 3B:
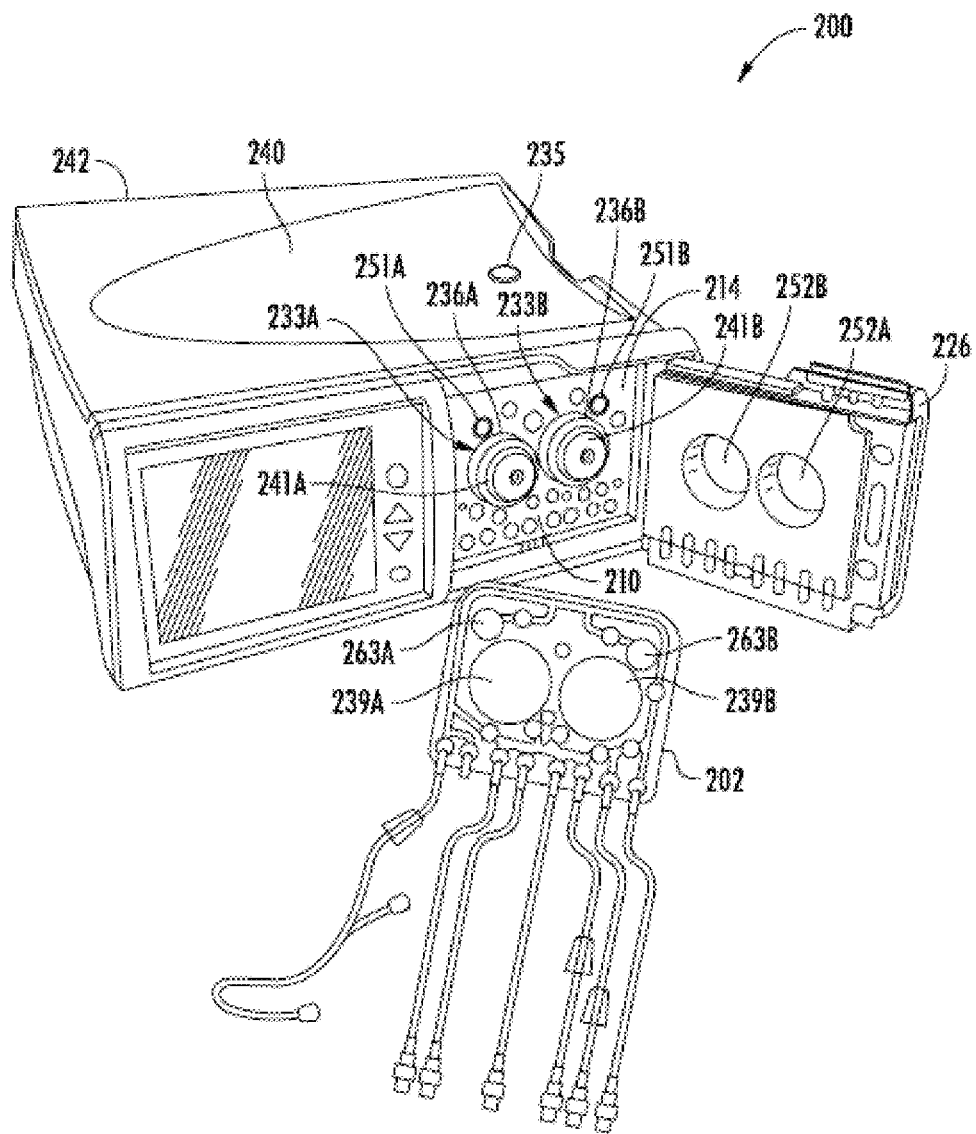

Referring now to FIGS. 3A and 3B, an example of an embodiment of a dialysis machine 200 is shown. The dialysis machine 200 may include the components described above with respect to the schematic of the system 100 and the machine 150 illustrated in FIGS. 1 and 2. The machine 200 may be configured to provide home dialysis treatment, for example, PD. In some implementations, the dialysis system and machine may be a home PD system, e.g., a PD system configured for use at a patient's home.

The dialysis machine 200 may include a housing 242, a door 226, and a cassette interface including pumps for contacting a cartridge or cassette 202 (used interchangeably without the intent to limit), where the cassette 202 is located within a cassette compartment 214 formed between the cassette interface and the closed door 226. Fluid lines (e.g., tubing) may be coupled to the cassette 202 in a known manner, such as via a connector, and may further include valves for controlling fluid flow to and from fluid bags including fresh dialysate and warming pouch. In some embodiments, when a cassette 202 is incorporated, at least a portion of the fluid lines (e.g., tubing) may be integral to the cassette 202. Prior to operation, a user may open the door 226 to insert a fresh cassette 202 and to remove the used cassette 202 after operation.

The cassette 202 may be placed in the cassette compartment 214 of the dialysis machine 200 for operation. The dialysis machine 200 may manage flowing dialysate into a patient's abdomen, and removal of the used dialysate and waste after a predetermined amount of time. During operation, dialysate fluid may be flowed into a patient's abdomen via the cassette 202, and spent dialysate, waste, and/or excess fluid may be removed from the patient's abdomen via the cassette 202.

While the dialysate is present in a peritoneal cavity of the patient, the dialysate may absorb contaminants and/or particulates from the patient's blood. PD uses the patient's peritoneum in the abdomen as a membrane across which fluids and dissolved substances (e.g., electrolytes, urea, glucose, albumin, osmotically active particles, and other small molecules) are exchanged from the blood. PD for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

The dialysis machine 200 may operate the pumps (as will be described in greater detail below) to move the fluid. In use, the pumps apply force to the cassette 202, that connect a fluid reservoir, e.g., dialysate bags to a catheter at the patient's peritoneum. By operation of the pumps, fresh dialysate may be introduced into the patient's peritoneum. Likewise, the pumps may draw fluid from the patient's peritoneum into a fluid reservoir or drain to waste. Multiple dialysate bags may be used including a clean fluid reservoir and a waste fluid reservoir. Operation of the pumps in conjunction with valves controls delivery or retrieval of fluid.

In connection with PD machine 200, the heating element 152 may be in the form of a heater tray 240 including a heating element 235 positioned, for example, on top of the housing 242 of the dialysis machine 200. The heater tray 240 may be any size and shape to accommodate a bag of dialysate (e.g., a 5L bag of dialysate) for batch heating. In use, for example as illustrated in the example embodiment of FIG. 3A, dialysate bags 234 may be suspended from hooks on the sides of a cart 244, and a heater bag 237 may be positioned in the heater tray 240. Connectors and tubing ports may connect the dialysate bags 234 and lines for transferring dialysate. Dialysate from the dialysate bags 234 may be transferred to the heater bag 237 in batches. For example, a batch of dialysate may be transferred from one or more dialysate bags 234 to the heater bag 237, where the dialysate is heated by the heating element 235. When the batch of dialysate has reached a predetermined temperature (e.g., approximately 98°-100° F., 37° C.), the batch of dialysate may be flowed into the patient. The dialysate bags 234 and the heater bag 237 may be connected to the cassette 202 via dialysate bag lines or tubing 238 and a heater bag line or tubing 238, respectively. The dialysate bag lines 238 may be used to pass dialysate from dialysate bags 234 to the cassette 202 during use, and a heater bag line 246 may be used to pass dialysate back and forth between the cassette 202 and the heater bag 237 during use. In addition, a patient line 248 and a drain line 250 may be connected to the cassette 202. The patient line 248 may be connected to a patient's abdomen via a catheter and may be used to pass dialysate back and forth between the cassette 202 and the patient's peritoneal cavity by the pumps during use. The drain line 250 may be connected to a drain or drain receptacle and may be used to pass dialysate from the cassette 202 to the drain or drain receptacle during use.

Referring to FIG. 3B, a more detailed view of the cassette interface 210 of the dialysis machine 200 is shown. As shown, in one embodiment, the PD machine 200 includes pumps or pumping mechanisms, which include pistons 233A, 233B with pump heads 241A, 241B attached to piston shafts that can be axially moved within piston access ports 236A, 236B formed in the cassette interface 210. In one embodiment, the piston shafts are connected to stepper motors that can be operated to move the pistons 233A, 233B axially inward and outward such that the pump heads 241A, 241B move axially inward and outward within the piston access ports 236A, 236B. In one embodiment, the stepper motors drive lead screws, which move nuts inward and outward along the lead screws. The nuts, in turn, are connected to the pistons 233A, 233B and thus cause the pistons 233A, 233B to move inward and outward as the stepper motors rotate the lead screws. Stepper motor controllers provide the necessary current to be driven through the windings of the stepper motors to move the pistons 233A, 233B. The polarity of the current determines whether the pistons 233A, 233B are advanced or retracted.

The PD machine 200 may also include encoders (e.g., optical encoders) that measure the rotational movement of the lead screws. The axial positions of the pistons 233A, 233B can be determined based on the rotational movement of the lead screws, as determined by the encoders. Thus, the measurements of the encoders can be used to accurately position the pump heads 241A, 241B of the pistons 233A, 233B.

In use, when the cassette 202 is properly positioned within the cassette compartment 214 of the PD machine 200 with the door 226 closed, the pump heads 241A, 241B of the PD machine 200 align with pump chambers 239A, 239B of the cassette 202 such that the pump heads 241A, 241B can be mechanically connected to dome-shaped fastening members of the cassette 202 overlying the pump chambers 239A, 239B. As a result of this arrangement, movement of the pump heads 241A, 241B toward the cassette 202 during treatment can decrease the volume of the pump chambers 239A, 239B and force dialysate out of the pump chambers 239A, 239B, while retraction of the pump heads 241A, 241B away from the cassette 202 can increase the volume of the pump chambers 239A, 239B and cause dialysate to be drawn into the pump chambers 239A, 239B.

As shown in FIG. 3B, the cassette interface 210 may also include pressure sensors 251A, 251B that align with pressure sensing chambers 263A, 263B of the cassette 202 when the cassette 202 is positioned within the cassette compartment 214. When included, portions of a membrane of the cassette 202 that overlie the pressure sensing chambers 263A, 263B adhere to the pressure sensors 251A, 251B using vacuum pressure. Specifically, clearance around the pressure sensors 251A, 251B communicates vacuum to the portions of the cassette membrane overlying the pressure sensing chambers 263A, 263B to hold those portions of the cassette membrane tightly against the pressure sensors 251A, 251B. The pressure of fluid within the pressure sensing chambers 263A, 263B causes the portions of the cassette membrane overlying the pressure sensing chambers 263A, 263B to contact and apply pressure to the pressure sensors 251A, 251B. The pressure sensors 251A, 251B can be any sensors that are capable of sensing the fluid pressure in the sensing chambers 263A, 263B.

The PD machine 200 may also include inflatable members (not shown) positioned within inflatable member ports (not shown) in the cassette interface 210. The inflatable members align with depressible dome regions of the cassette 202 when the cassette 202 is positioned within the cassette compartment 214 of the PD machine 200. The inflatable members act as valves to direct dialysate through the cassette 202 in a desired manner during use. In particular, the inflatable members bulge outward beyond the surface of the cassette interface 210 and into contact with the depressible dome regions of the cassette 202 when inflated, and retract into the inflatable member ports and out of contact with the cassette 202 when deflated. By inflating certain inflatable members to depress their associated dome regions on the cassette 202, certain fluid flow paths within the cassette 202 can be occluded. Thus, dialysate can be pumped through the cassette 202 by actuating the pump heads 241A, 241B, and can be guided along desired flow paths within the cassette 202 by selectively inflating and deflating the various inflatable members.

The PD machine 200 may also include locating pins extending from the cassette interface 210. When the door 226 is in the open position, the cassette 202 can be loaded onto the cassette interface 210 by positioning the top portion of the cassette 202 under the locating pins and pushing the bottom portion of the cassette 202 toward the cassette interface 210. The cassette 202 is dimensioned to remain securely positioned between the locating pins and a spring loaded latch extending from the cassette interface 210 to allow the door 226 to be closed over the cassette 202. The locating pins help to ensure that proper alignment of the cassette 202 within the cassette compartment 214 is maintained during use.

As shown, the door 226 may include cylindrical recesses 252A, 252B that substantially align with the pistons 233A, 233B when the door 226 is in the closed position. When the cassette 202 is positioned within the cassette compartment 214, hollow projections (not shown) of the cassette 202, inner surfaces of which partially define the pump chambers 239A, 239B, fit within the recesses 252A, 252B. The door 226 may further include a pad that is inflated during use to compress the cassette 202 between the door 226 and the cassette interface 210. With the pad inflated, the portions of the door 226 forming the recesses 252A, 252B support the projections of the cassette 202 and the planar surface of the door 226 supports the other regions of the cassette 202. The door 226 can counteract the forces applied by the inflatable members and thus allows the inflatable members to actuate the depressible dome regions on the cassette 202. The engagement between the door 226 and the hollow projections of the cassette 202 can also help to hold the cassette 202 in a desired fixed position within the cassette compartment 214 to further ensure that the pistons 233A, 233B align with the fluid pump chambers 239A, 239B of the cassette 202.

In use, the controller is connected to the pressure sensors 251A, 251B, to the stepper motors (e.g., the drivers of the stepper motors) that drive the pistons 233A, 233B, and to the encoders that monitor rotation of the lead screws of the stepper motors such that the controller can receive signals from and transmit signals to those components of the system. In use, the controller monitors the components to which it is connected to determine whether any complications exists within the PD system 100. In the event of complications, the controller can trigger one or more alarms and initiates communication (e.g., wirelessly) to activate one or more of the peripheral devices. The peripheral devices can, for example, be activated in a manner to get the attention of the patient and/or to draw the attention of the patient to a region of the PD system 100 determined to be experiencing the complication. Additional information and details on the operation of the PD machine including the pumps is disclosed in United States Published Patent Application No. 2015/0025449, filed on Jul. 22, 2013, entitled Activating Peripheral Devices in a Dialysis System, the entire contents of which are incorporated by reference herein.

One disadvantage of current dialysis machines, in particular, PD machines that are commonly used in patient's homes, is that the housing 242 of the dialysis machine 200 may become infested with bugs, which may adversely affect the operation of the dialysis machine 200 and, in any event, require cleaning of the dialysis machine 200. To this end, in order to avoid bug infestation, in accordance with one or more features of the present disclosure, the dialysis machine may include an ultrasonic high frequency generator and emitter arranged and configured to generate and transmit an ultrasonic high frequency sound. In use, the emitted high frequency sound is inaudible to humans. However, in use, the emitted high frequency sound is audible by bugs such as, for example, insects, spiders, roaches, etc. Thus arranged, the emitted high frequency sound is incapable of being heard by humans however, the emitted high frequency sound is arranged and configured to repel bugs and thus prevents (e.g., discourages) bugs from entering and infesting the housing 242 of the dialysis machine 200. In some embodiments, the emitted high frequency sound may be directed towards other components within the dialysis system to help prevent bug infestation. For example, the ultrasonic high frequency sound may be directed toward the dialysate bags, tubing, heat source (a warming pouch, a heating chamber, etc.) and/or the like.

In addition, advantageously, the emitted high frequency sound is capable of expelling or repelling bugs from a dialysis device in a manner that does not require user intervention, maintenance, and/or chemicals.

In one embodiment, the emitted high frequency sound may have any suitable frequency that is inaudible by humans while being audible by bugs such that bugs are repelled by the emitted high frequency sound. In one embodiment, the emitted high frequency sound may be between 20 kHz and 120 kHz. The following are some example frequency ranges: the emitted high frequency sound may have various frequencies. For example, the emitted high frequency sound may have a frequency of about 20 kHz to about 120 kHz. In other examples, the emitted high frequency sound may have a frequency of about 20 kHz, 25 kHz, 30 kHz, 40 kHz, 50 kHz, 60 kHz, 70 kHz, 80 kHz, 90 kHz, 100 kHz, 120 kHz, and any value or range between any two of these values (including endpoints).

Figure 4:
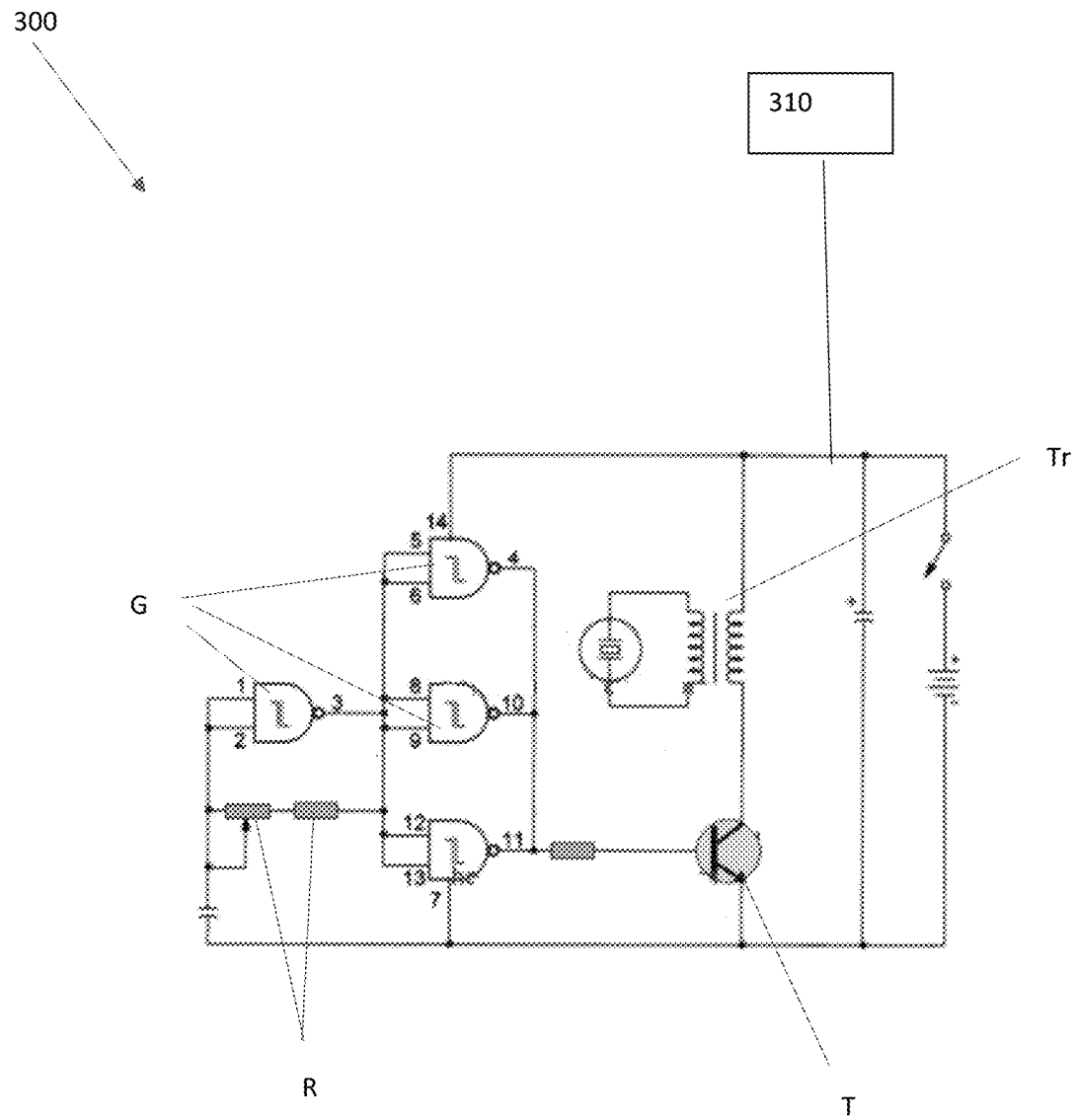
FIG. 4 illustrates an example embodiment of a circuit that can be used in the dialysis machine of FIGS. 1-3, the circuit arranged and configured to generate and emit an ultrasonic high frequency sound arranged and configured to repel bugs in accordance with one or more features of the present disclosure.

In one embodiment, the emitted high frequency sound may be generated and emitted by any suitable device now known or hereafter developed. For example, in one embodiment, the emitted high frequency sound may be generated and emitted by an electronic circuit. The electronic circuit may be provided in any suitable form now known or hereafter developed. For example, with reference to FIG. 4, the electronic circuit 300 may be provided as a stand-alone circuit printed on a stand-alone circuit board arranged and configured to generate and emit a high frequency sound. In one embodiment, the stand-alone circuit board may be coupled to one or more alternate circuit boards of the dialysis machine 200. Alternatively, however, it is envisioned that the electronic circuit may be embedded or incorporated into one of the existing circuit boards of the dialysis machine (e.g., the electronic circuit for generating and emitting the ultrasonic high frequency sound may be incorporated into an existing circuit board of the dialysis machine 200).

In one embodiment, by arranging the electronic circuit 300 as a stand-alone circuit printed on a stand-alone circuit board, the circuit board can be the same for any medical device or dialysis machine. In use, the stand-alone circuit board may include a power source to keep the circuit functional such as, for example, a rechargeable battery, which can be recharged once the medical device or dialysis machine is powered ON. In one embodiment, the circuit board may be centrally located within the medical device or dialysis machine to provide all around protection. In one embodiment, the circuit may include a plurality of generators and/or emitters depending on the power of emitter and the size of the medical device or dialysis machine.

As illustrated, in one embodiment, the electronic circuit 300 may include a series or components arranged and configured to generate and emit the ultrasonic high frequency sound. For example, the electronic circuit 300 may include one or more resistors R, N and gates G, transistors T, transformers Tr, and any other circuits or components needed to generate and emit the ultrasonic high frequency sound.

In one embodiment, the electronic circuit 300 is continuously powered so that the electronic circuit 300 is continuously active and thus continuously emitting an ultrasonic high frequency sound at all times (e.g., the electronic circuit 300 is arranged and configured to be active (i.e., emitting) at all times once activated). For example, in one embodiment, the electronic circuit 300 may be coupled to a rechargeable power supply or battery. In use, the rechargeable power source or battery is arranged and configured to continuously power the electronic circuit 300 so that the ultrasonic high frequency sound is continuously emitted. In use, the rechargeable power supply or battery may be charged by the dialysis machine 200 when the dialysis machine 200 is powered ON and/or activated. Alternatively, however, the electronic circuit 300 may be powered by other mechanisms including, for example, intermittently powered by the dialysis machine 200 when the dialysis machine 200 is powered ON and/or activated.

In one embodiment, the electronic circuit 300 is coupled to the controller (e.g., controller 155) so that the electronic circuit 300 can be controlled via, for example, software, circuitry, and/or other controlling element. In some embodiments for example, the controlling element may operate to adjust the frequency of the emitted ultrasonic high frequency sound. In various embodiments, a user, patient, and/or the like may provide information to the system indicating bugs of interest that may be a source of known infestation (e.g., flies) for a particular location of use. The frequency of the emitted ultrasonic high frequency sound may be selected to be in a range known to be effective for the highlighted bugs. In another example, the frequency may be selected (by default, for instance) to be directed to bugs known to be attracted to dialysate, etc.

In one embodiment, the emitter is arranged and configured to be powerful enough to prevent infestation. In addition, in one embodiment, the circuit board may be arranged and configured with a sensor such as, for example, a motion sensor to detect the presence of bugs. In use, when motion is detected such as, for example, inside of the housing, the ultrasonic generator and emitter may be activated. In addition, and/or alternatively, in one embodiment, the ultrasonic generator and emitter may be arranged and configured to cycle through different frequency levels so that bugs don't get accustomed to a single frequency.

As previously mentioned, in a preferred embodiment, the ultrasonic high frequency sound may be continuously emitted. However, in various alternate embodiments, the ultrasonic high frequency generator and emitter may be selectively turned ON and OFF. For example, the controlling element may operate to turn the high frequency generator and emitter ON/OFF. For example, the high frequency generator and emitter may be controlled to only emit ultrasonic high frequency sound at certain times, such as, for example, during a dialysis treatment, or when the dialysis machine is powered ON, but not active in a dialysis treatment, or during a certain duration before and/or after a dialysis treatment, or based on user preference, user behavior, and/or the like. For example, a user may have an overnight PD dialysis treatment that is scheduled to start at 10:00 pm (or that typically starts at 10:00 pm based on historical use patterns) and the controlling element may operate to control the high frequency generator and emitter to generate a ultrasonic high frequency sound for a duration of 1 hour prior to the start of the treatment (i.e., starting at 9:00 pm and ending at 10:00 pm). In another example, the ultrasonic high frequency sound may be controlled to be emitted for a certain duration (e.g., 30 minutes) at certain time intervals (e.g., every 2 hours) to conserve power, etc.

Various features described herein have been explained in connection with the dialysis machine 200 having a particular configuration. It is contemplated that the various features described herein may be used with dialysis machines having other configurations, for example, different types of dialysis machines and/or dialysis machines having other configurations. The system described herein may be used with any appropriate dialysis machine and/or other medical devices including hemodialysis machines.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A dialysis machine for conducting a dialysis treatment on a patient, the dialysis machine comprising:
   a dialysate source;
   a fluid pump in fluid communication with the dialysate source and the patient;
   a housing including an ultrasonic high frequency generator and emitter arranged and configured to generate and transmit an ultrasonic high frequency sound to repel bugs to prevent bugs from entering and infesting the housing of the dialysis machine; and
   a controller:
      configured to carry out the dialysis treatment on the patient via the dialysis machine, the fluid pump activated during at least a portion of the dialysis treatment to transfer dialysate from the dialysate source to the patient, and
      coupled to the ultrasonic high frequency generator and emitter, the controller to turn the ultrasonic high frequency generator and emitter ON when the dialysis machine is not being used in the dialysis treatment.

2. The dialysis machine of claim 1, wherein the emitted ultrasonic high frequency sound is inaudible to humans but audible by bugs.

3. The dialysis machine of claim 1, wherein the emitted ultrasonic high frequency sound is between 20 kHz and 120 kHz.

4. The dialysis machine of claim 1, wherein the ultrasonic high frequency generator and emitter is an electronic circuit.

5. The device dialysis machine of claim 1, wherein the ultrasonic high frequency generator and emitter is an electronic circuit printed on a stand-alone circuit board arranged and configured to be coupled to a circuit board of the dialysis machine, the stand-alone circuit board centrally located within the dialysis machine.

6. The dialysis machine of claim 1, wherein the ultrasonic high frequency generator and emitter is coupled to a rechargeable battery.

7. The dialysis machine of claim 6, wherein the rechargeable battery is arranged and configured to be charged by a power source of the dialysis machine when the dialysis machine is powered ON.

8. The dialysis machine of claim 1 wherein the ultrasonic high frequency generator and emitter is coupled to the controller of the dialysis machine so that a frequency of the emitted ultrasonic high frequency sound is adjustable.

9. A method of repelling bug infestation in a dialysis machine, comprising:
   continuously powering an ultrasonic high frequency generator and emitter;
   determining an operational state of the dialysis machine, the operational state indicating whether the dialysis machine is active in a dialysis treatment transferring dialysate to a patient;
   turning the ultrasonic high frequency generator and emitter ON to emit, from a housing of the dialysis machine, an ultrasonic high frequency sound to repel bugs from entering and infesting the housing of the dialysis machine when the state information indicates that the dialysis machine is not active in the dialysis treatment; and
   turning the ultrasonic high frequency generator OFF when the state information indicates that the dialysis machine is active in the dialysis treatment.

10. The method of claim 9, wherein the emitted ultrasonic high frequency sound is between 20 kHz and 120 kHz.

11. The dialysis machine of claim 1, wherein the ultrasonic high frequency generator and emitter is configured to cycle through multiple frequencies during operation.

12. The dialysis machine of claim 1, wherein the ultrasonic high frequency generator and emitter is arranged and configured to generate and transmit the ultrasonic high frequency sound toward at least one of a warming pouch or a heating chamber of the dialysis machine.

13. The dialysis machine of claim 1, the controller configured to:
   access infestation information indicating bugs of interest, and
   select the emitted ultrasonic high frequency sound based on at least one bug of the bugs of interest.

14. The method of claim 9, further comprising:
   accessing infestation information indicating bugs of interest, and
   selecting the emitted ultrasonic high frequency sound based on at least one bug of the bugs of interest.

15. The dialysis machine of claim 1, wherein the controller is configured to:
   access state information provided by the dialysis machine, the state information providing a status of operations of the dialysis machine, the status of operations comprising at least one of trigger pump, ready to execute, executing, or completed, and
   turn the ultrasonic high frequency generator and emitter ON based on the state information indicating that the dialysis machine is not being used in the dialysis treatment.

16. The dialysis machine of claim 1, wherein the controller is configured to:
  determine a future scheduled time of the dialysis treatment,
  turn the ultrasonic high frequency generator and emitter ON for a specified duration before the future scheduled time and OFF after the specified duration and prior to the future scheduled time.

17. The method of claim 9, further comprising:
  determining a future scheduled time of the dialysis treatment,
  turning the ultrasonic high frequency generator and emitter ON for a specified duration before the future scheduled time and OFF after the specified duration and prior to the future scheduled time.

18. A peritoneal dialysis (PD) system for conducting a dialysis treatment on a patient, the PD system comprising:
  a dialysate source;
  a fluid pump in fluid communication with the dialysate source and the patient;
  a memory storing instructions for performing the dialysis treatment and timing for the dialysis treatment;
  a controller operatively coupled to the memory and the fluid pump, the controller configured to carry out the dialysis treatment on the patient via activating the fluid pump during at least a portion of the dialysis treatment to transfer dialysate from the dialysate source to the patient; and
  a housing including an ultrasonic high frequency generator and emitter arranged and configured to generate and transmit an ultrasonic high frequency sound to repel bugs to prevent bugs from entering and infesting the housing of the dialysis machine,
  wherein:
    the timing for the dialysis treatment includes a future scheduled time of the dialysis treatment, and
    the controller is configured to turn the ultrasonic high frequency generator and emitter ON for a specified duration before the future scheduled time and OFF after the specified duration and prior to the future scheduled time.

19. The PD system of claim 18, wherein the timing for the dialysis treatment is determined based on historical use patterns of the PD system.

20. The PD system of claim 18, wherein the ultrasonic high frequency generator and emitter is coupled to a rechargeable battery arranged and configured to be charged by a power source of the PD system when the medical device dialysis machine is powered ON.

* * * * *